(12) United States Patent
Jenkins et al.

(10) Patent No.: US 7,182,764 B2
(45) Date of Patent: Feb. 27, 2007

(54) STEERABLE LOOP STRUCTURES FOR SUPPORTING DIAGNOSTIC AND THERAPEUTIC ELEMENTS IN CONTACT WITH BODY TISSUE

(75) Inventors: Thomas R. Jenkins, Oakland, CA (US); David K. Swanson, Campbell, CA (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 0 days.

(21) Appl. No.: 11/130,857

(22) Filed: May 17, 2005

(65) Prior Publication Data

US 2005/0215992 A1    Sep. 29, 2005

Related U.S. Application Data

(62) Division of application No. 09/709,087, filed on Nov. 10, 2000, now Pat. No. 6,916,306.

(51) Int. Cl.
*A61B 18/18* (2006.01)

(52) U.S. Cl. .................. 606/41; 607/96; 604/95.04

(58) Field of Classification Search ............ 606/41; 607/96, 100, 101, 105; 604/113, 95.04, 95.01, 604/95.05
See application file for complete search history.

(56) References Cited

U.S. PATENT DOCUMENTS

| | | |
|---|---|---|
| 1,207,479 A | 12/1916 | Bisgaard |
| 4,033,331 A | 7/1977 | Guss et al. |
| 4,181,131 A | 1/1980 | Ogiu |
| 4,245,624 A | 1/1981 | Komiya |
| 4,753,223 A | 6/1988 | Bremer |
| 4,826,087 A | 5/1989 | Chinery |
| 5,041,085 A | 8/1991 | Osbourne |
| 5,098,412 A | 3/1992 | Shiu |
| 5,156,151 A | 10/1992 | Imran |
| 5,263,493 A | 11/1993 | Avitall |
| 5,273,535 A | 12/1993 | Edwards |
| 5,306,245 A | 4/1994 | Heaven |
| 5,368,592 A | 11/1994 | Stern |
| 5,399,165 A | 3/1995 | Paul, Jr. |
| 5,415,656 A | 5/1995 | Tihon et al. |
| 5,437,665 A | 8/1995 | Munro |
| 5,439,006 A | 8/1995 | Brennen |
| 5,482,037 A | 1/1996 | Borghi |
| 5,487,385 A | 1/1996 | Avitall |
| 5,549,661 A | 8/1996 | Kordis |
| 5,571,088 A | 11/1996 | Lennox |
| 5,582,609 A | 12/1996 | Swanson |
| 5,637,090 A | 6/1997 | McGee |
| 5,656,029 A | 8/1997 | Imran et al. |
| 5,702,368 A | 12/1997 | Stevens |
| 5,702,438 A | 12/1997 | Avitall |

(Continued)

FOREIGN PATENT DOCUMENTS

DE    3920707 A1    1/1991

(Continued)

*Primary Examiner*—Rosiland Rollins
(74) *Attorney, Agent, or Firm*—Henricks, Slavin & Holmes LLP

(57) ABSTRACT

A probe that includes a elongate body and a steerable loop structure that supports electrodes or other operative elements against the body tissue.

20 Claims, 5 Drawing Sheets

U.S. PATENT DOCUMENTS

| | | | |
|---|---|---|---|
| 5,709,224 A | 1/1998 | Behl |
| 5,730,127 A | 3/1998 | Avitall |
| 5,738,683 A | 4/1998 | Osypka |
| 5,782,239 A | 7/1998 | Webster |
| 5,782,899 A | 7/1998 | Imran |
| 5,800,482 A | 9/1998 | Pomeranz |
| 5,800,484 A | 9/1998 | Gough |
| 5,820,591 A | 10/1998 | Thompson |
| 5,836,947 A | 11/1998 | Fleischman |
| 5,863,291 A | 1/1999 | Schaer |
| 5,871,523 A | 2/1999 | Fleischman |
| 5,879,295 A | 3/1999 | Li |
| 5,882,333 A | 3/1999 | Schaer |
| 5,895,417 A | 4/1999 | Pomeranz |
| 5,910,129 A | 6/1999 | Koblish |
| 5,971,983 A | 10/1999 | Lesh |
| 6,007,531 A | 12/1999 | Snoke |
| 6,012,457 A | 1/2000 | Lesh |
| 6,016,811 A | 1/2000 | Knopp |
| 6,048,329 A | 4/2000 | Thompson |
| 6,064,902 A | 5/2000 | Haissaguerre |
| 6,071,274 A | 6/2000 | Thompson |
| 6,071,279 A | 6/2000 | Whayne |
| 6,071,281 A | 6/2000 | Burnside |
| 6,120,500 A | 9/2000 | Bednarek |
| 6,146,355 A | 11/2000 | Biggs |
| 6,161,543 A | 12/2000 | Cox |
| 6,190,382 B1 | 2/2001 | Ormsby |
| 6,203,525 B1 | 3/2001 | Whayne |
| 6,214,002 B1 | 4/2001 | Fleischman |
| 6,217,528 B1 | 4/2001 | Koblish |
| 6,237,605 B1 | 5/2001 | Vaska |
| 6,311,692 B1 | 11/2001 | Vaska |
| 6,314,962 B1 | 11/2001 | Vaska |
| 6,314,963 B1 | 11/2001 | Vaska |
| 6,332,880 B1 | 12/2001 | Yang |
| 6,402,746 B1 | 6/2002 | Whayne |
| 6,413,234 B1 | 7/2002 | Thompson |
| 6,454,758 B1 | 9/2002 | Thompson |
| 6,464,700 B1 | 10/2002 | Koblish |
| 6,529,756 B1 | 3/2003 | Phan |
| 6,542,781 B1 | 4/2003 | Koblish |
| 6,607,505 B1 | 8/2003 | Thompson |
| 6,613,046 B1 | 9/2003 | Jenkins |
| 6,645,199 B1 | 11/2003 | Jenkins |
| 6,916,306 B1 | 7/2005 | Jenkins et al. |
| 7,025,766 B2 | 4/2006 | Whayne |
| 7,029,471 B2 | 4/2006 | Thompson |

FOREIGN PATENT DOCUMENTS

| | | |
|---|---|---|
| EP | 0238106 A1 | 9/1987 |
| EP | 0737487 A2 | 10/1996 |
| EP | 0868922 A2 | 10/1998 |
| EP | 0916360 A2 | 5/1999 |
| WO | WO-98/26724 A1 | 6/1998 |
| WO | WO-99/05971 A1 | 2/1999 |

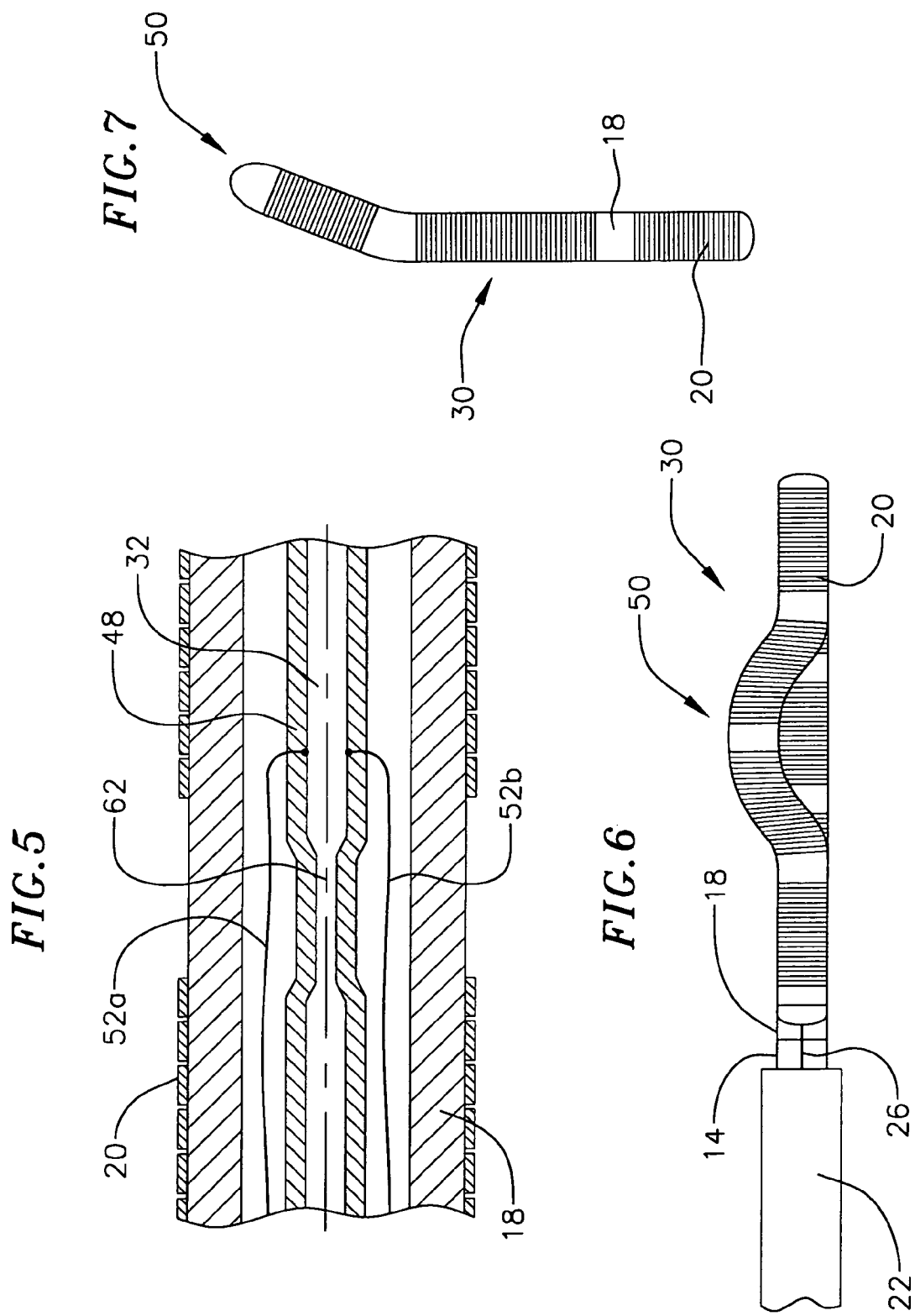

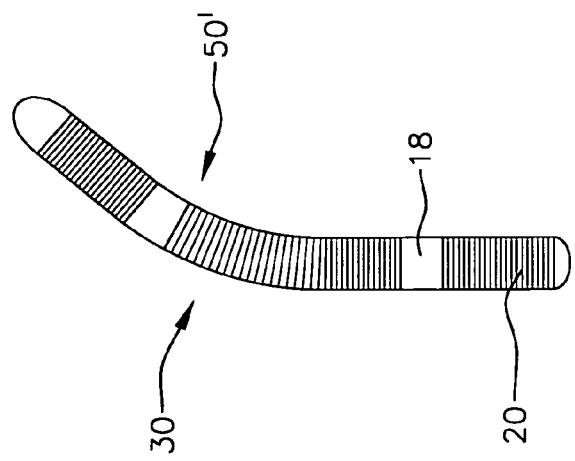
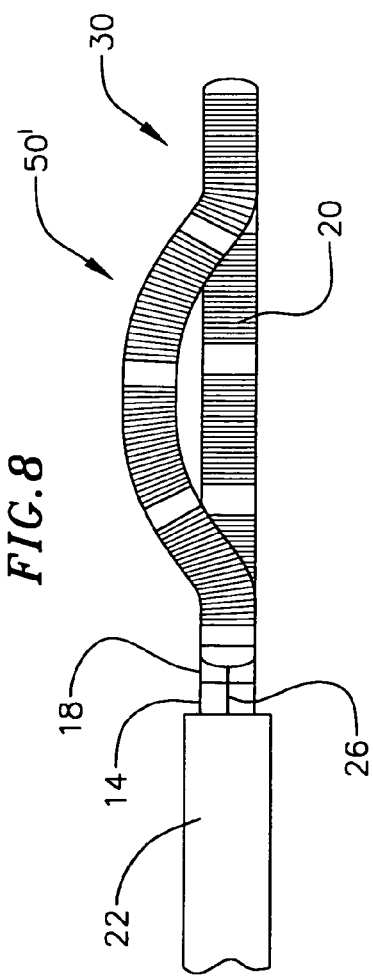
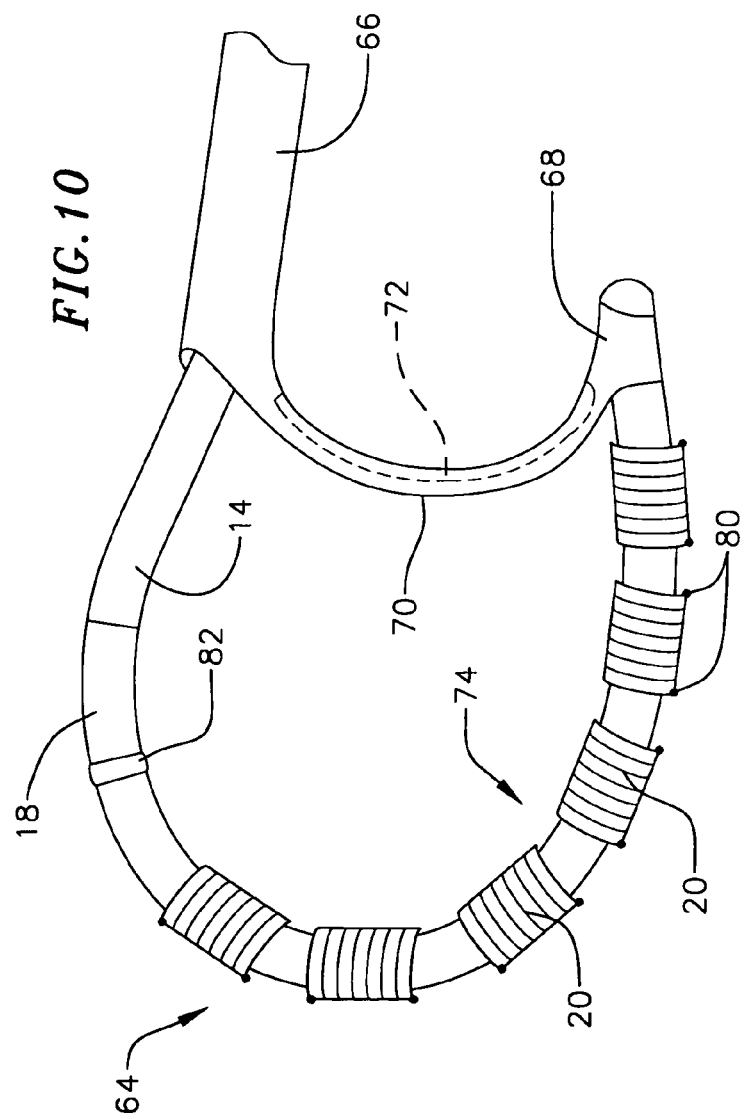

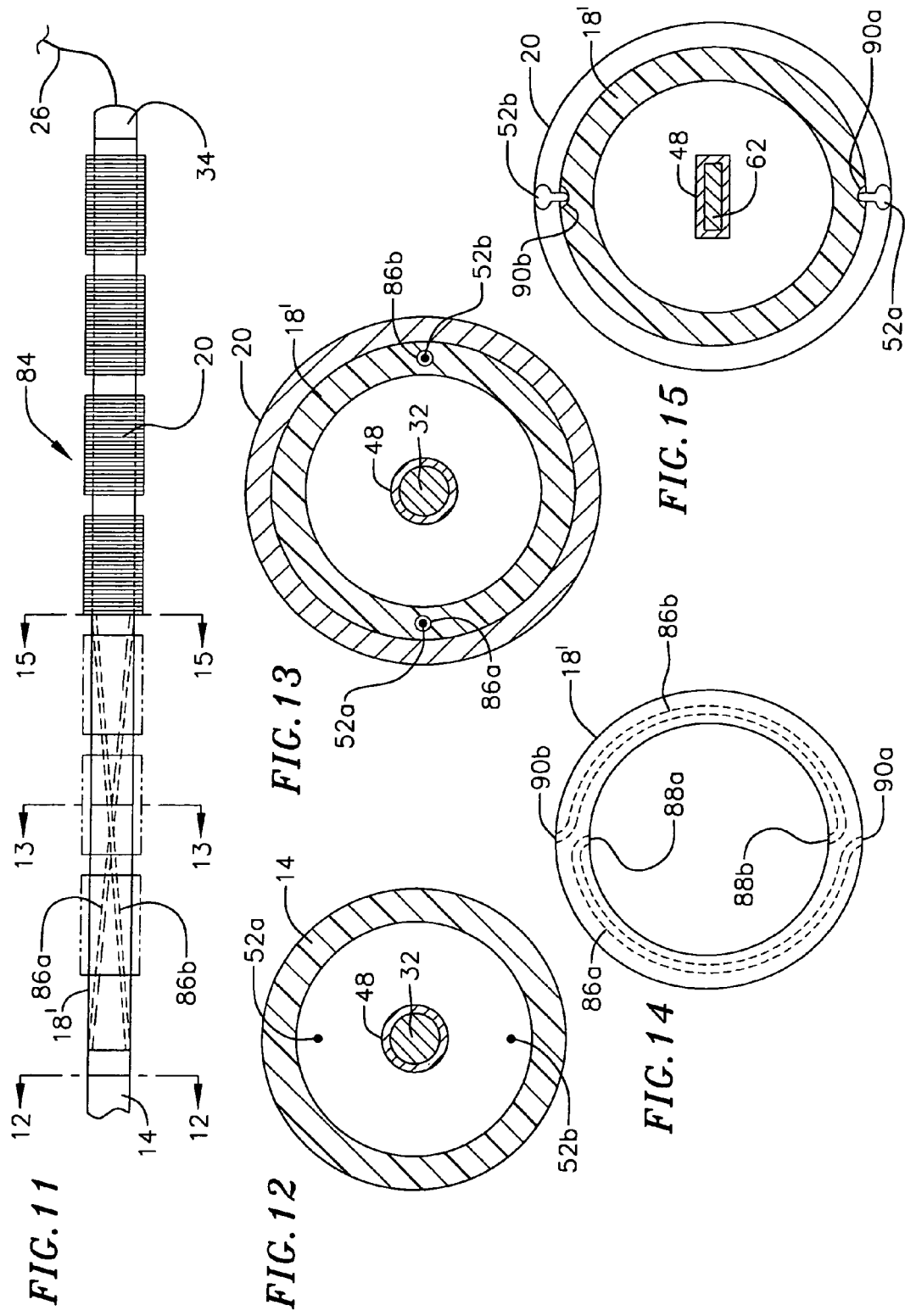

STEERABLE LOOP STRUCTURES FOR SUPPORTING DIAGNOSTIC AND THERAPEUTIC ELEMENTS IN CONTACT WITH BODY TISSUE

CROSS-REFERENCE TO RELATED APPLICATIONS

This application is a divisional of U.S. application Ser. No. 09/709,087, filed Nov. 10, 2000, now U.S. Pat. No. 6,916,306.

BACKGROUND OF THE INVENTIONS

1. Field of Inventions

The present inventions relate generally to medical devices that support one or more diagnostic or therapeutic elements in contact with body tissue and, more particularly, to loop structures that support one or more diagnostic or therapeutic elements in contact with body tissue.

2. Description of the Related Art

There are many instances where diagnostic and therapeutic elements must be inserted into the body. One instance involves the treatment of cardiac conditions such as atrial fibrillation and atrial flutter which lead to an unpleasant, irregular heart beat, called arrhythmia.

Normal sinus rhythm of the heart begins with the sinoatrial node (or "SA node") generating an electrical impulse. The impulse usually propagates uniformly across the right and left atria and the atrial septum to the atrioventricular node (or "AV node"). This propagation causes the atria to contract in an organized way to transport blood from the atria to the ventricles, and to provide timed stimulation of the ventricles. The AV node regulates the propagation delay to the atrioventricular bundle (or "HIS" bundle). This coordination of the electrical activity of the heart causes atrial systole during ventricular diastole. This, in turn, improves the mechanical function of the heart. Atrial fibrillation occurs when anatomical obstacles in the heart disrupt the normally uniform propagation of electrical impulses in the atria. These anatomical obstacles (called "conduction blocks") can cause the electrical impulse to degenerate into several circular wavelets that circulate about the obstacles. These wavelets, called "reentry circuits," disrupt the normally uniform activation of the left and right atria.

Because of a loss of atrioventricular synchrony, the people who suffer from atrial fibrillation and flutter also suffer the consequences of impaired hemodynamics and loss of cardiac efficiency. They are also at greater risk of stroke and other thromboembolic complications because of loss of effective contraction and atrial stasis.

One surgical method of treating atrial fibrillation by interrupting pathways for reentry circuits is the so-called "maze procedure" which relies on a prescribed pattern of incisions to anatomically create a convoluted path, or maze, for electrical propagation within the left and right atria. The incisions direct the electrical impulse from the SA node along a specified route through all regions of both atria, causing uniform contraction required for normal atrial transport function. The incisions finally direct the impulse to the AV node to activate the ventricles, restoring normal atrioventricular synchrony. The incisions are also carefully placed to interrupt the conduction routes of the most common reentry circuits. The maze procedure has been found very effective in curing atrial fibrillation. However, the maze procedure is technically difficult to do. It also requires open heart surgery and is very expensive.

Maze-like procedures have also been developed utilizing catheters which can form lesions on the endocardium (the lesions being 1 to 15 cm in length and of varying shape) to effectively create a maze for electrical conduction in a predetermined path. The formation of these lesions by soft tissue coagulation (also referred to as "ablation") can provide the same therapeutic benefits that the complex incision patterns that the surgical maze procedure presently provides, but without invasive, open heart surgery.

Catheters used to create lesions typically include a relatively long and relatively flexible body portion that has a soft tissue coagulation electrode on its distal end and/or a series of spaced tissue coagulation electrodes near the distal end. The portion of the catheter body portion that is inserted into the patient is typically from 23 to 55 inches in length and there may be another 8 to 15 inches, including a handle, outside the patient. The length and flexibility of the catheter body allow the catheter to be inserted into a main vein or artery (typically the femoral artery), directed into the interior of the heart, and then manipulated such that the coagulation electrode contacts the tissue that is to be ablated. Fluoroscopic imaging is used to provide the physician with a visual indication of the location of the catheter.

In some instances, the proximal end of the catheter body is connected to a handle that includes steering controls. Exemplary catheters of this type are disclosed in U.S. Pat. No. 5,582,609. In other instances, the catheter body is inserted into the patient through a sheath and the distal portion of the catheter is bent into loop that extends outwardly from the sheath. This may be accomplished by pivotably securing the distal end of the catheter to the distal end of the sheath, as is illustrated in U.S. Pat. No. 6,071,279. The loop is formed as the catheter is pushed in the distal direction. The loop may also be formed by securing a pull wire to the distal end of the catheter that extends back through the sheath, as is illustrated in U.S. Pat. No. 6,048,329. Loop catheters are advantageous in that they tend to conform to different tissue contours and geometries and provide intimate contact between the spaced tissue coagulation electrodes (or other diagnostic or therapeutic elements) and the tissue. Loop catheters also tend to cause the atria to conform to the shape of the loop.

The inventor herein has determined that one issue associated with conventional catheters is that, when deployed, the loop structures tend to follow the path of least resistance and occupy the largest diameter portion of the atria. The largest diameter portion is not, however, always the intended diagnostic or therapeutic location. This is especially true in those instances where the preferred loop position is near an atrial appendage or a ventricular annulus because conventional loop structures can slip into the atrial appendage or ventricular annulus.

Accordingly, the inventor herein has determined that a need exists generally for loop structures that can be deployed within the atrium (or some other bodily structure) and, if desired, deflected in such a manner that they occupy a portion of the atrium other than the largest diameter portion.

SUMMARY OF THE INVENTION

Accordingly, the general object of the present inventions is to provide a device that avoids, for practical purposes, the aforementioned problems. In particular, one object of the present inventions is to provide a loop structure that can, if desired, be deployed with a bodily structure in such a manner that it occupies a portion of the bodily structure other than the largest diameter portion and/or the portion associated with the path of least resistance. Another object of the present inventions is to provide a loop structure having at least a portion that can, if desired, be deflected.

In order to accomplish some of these and other objectives, a probe in accordance with one embodiment of a present invention includes an elongate body that can be deployed as a loop and a steering element secured to the distal portion of the elongate body. When the loop is deployed in a loop plane, for example, the steering element may be used to deflect a portion of the loop out of the loop plane. Such a probe advantageously allows the physician to steer the loop into contact with intended diagnostic and therapeutic locations which the loop would not contact absent such steering. In an atrium, for example, the steering capability may be used by a physician to move a portion of the loop away from an atrial appendage located along the path of least resistance to a more desirable location.

The above described and many other features and attendant advantages of the present inventions will become apparent as the inventions become better understood by reference to the following detailed description when considered in conjunction with the accompanying drawings.

BRIEF DESCRIPTION OF THE DRAWINGS

Detailed description of preferred embodiments of the inventions will be made with reference to the accompanying drawings.

FIG. 5 is a section view of another portion of the distal region of the exemplary catheter illustrated in FIG. 1.

FIG. 6 is a top view of the distal region of the exemplary catheter illustrated in FIG. 1 with a portion steered out of the loop plane.

FIG. 7 is an end view of the distal region of the exemplary catheter illustrated in FIG. 1 with a portion steered out of the loop plane.

FIG. 8 is a top view of the distal region of another catheter in accordance with another preferred embodiment of a present invention with a portion steered out of the loop plane.

FIG. 9 is an end view of the exemplary catheter illustrated in FIG. 8.

FIG. 10 is a side view of the distal region of a catheter in accordance with still another preferred embodiment of a present invention.

FIG. 11 is a side view of the distal region of a catheter in accordance with yet another preferred embodiment of a present invention with some of the electrodes shown in phantom lines for clarity.

FIG. 12 is a section view taken along line 12—12 in FIG. 11.

FIG. 13 is a section view taken along line 13—13 in FIG. 11.

FIG. 14 is an end view of the distal member in the exemplary catheter illustrated in FIG. 11.

FIG. 15 is a section view taken along line 15—15 in FIG. 11.

DETAILED DESCRIPTION OF THE PREFERRED EMBODIMENTS

Figure 1:
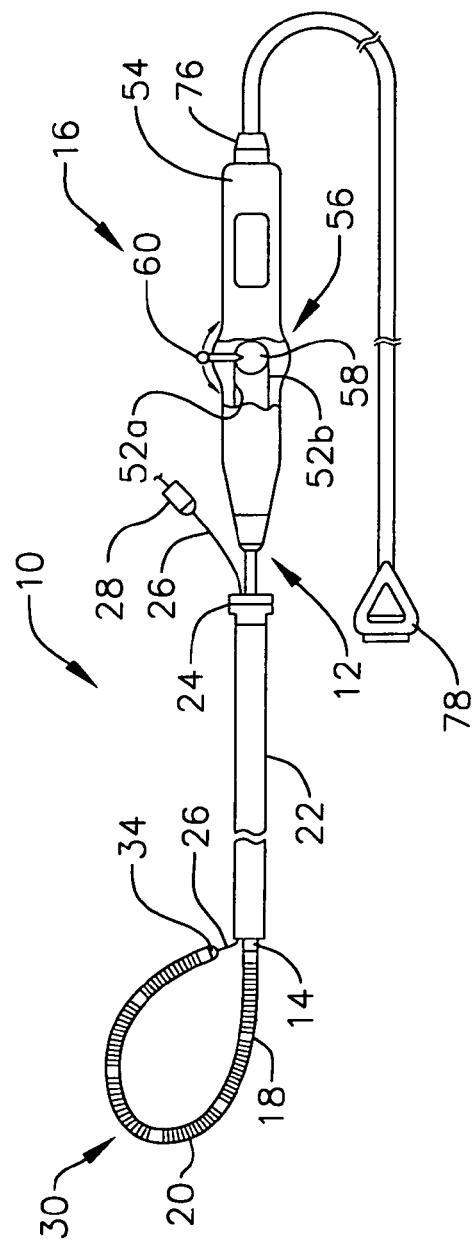
FIG. 1 is a side view of a catheter in accordance with a preferred embodiment of a present invention.

The following is a detailed description of the best presently known modes of carrying out the inventions. This description is not to be taken in a limiting sense, but is made merely for the purpose of illustrating the general principles of the inventions.

The detailed description of the preferred embodiments is organized as follows:

I. Introduction
II. Steerable Loop Structures
III. Electrodes, Temperature Sensing and Power Control The section titles and overall organization of the present detailed description are for the purpose of convenience only and are not intended to limit the present inventions.

I. Introduction

The present inventions may be used within body lumens, chambers or cavities for diagnostic or therapeutic purposes in those instances where access to interior bodily regions is obtained through, for example, the vascular system or alimentary canal and without complex invasive surgical procedures. For example, the inventions herein have application in the diagnosis and treatment of arrhythmia conditions within the heart. The inventions herein also have application in the diagnosis or treatment of ailments of the gastrointestinal tract, prostrate, brain, gall bladder, uterus, and other regions of the body.

With regard to the treatment of conditions within the heart, the present inventions are designed to produce intimate tissue contact with target substrates associated with various arrhythmias, namely atrial fibrillation, atrial flutter, and ventricular tachycardia. For example, embodiments of the present inventions, which may include diagnostic and/or soft tissue coagulation electrodes, can be used to map tissue and/or create lesions in tissue that cure arrhythmias.

Although the present inventions are discussed primarily in the context of catheter-based probes, the inventions are also adaptable for use with probes other than catheter-based probes. For example, the structures disclosed herein may be used in conjunction with hand held surgical devices (or "surgical probes"). The distal end of a surgical probe may be placed directly in contact with the targeted tissue area by a physician during a surgical procedure, such as open heart surgery. Here, access may be obtained by way of a thoracotomy, median sternotomy, or thoracostomy. Exemplary surgical probes are disclosed in U.S. Pat. No. 6,071,281, which is incorporated herein by reference.

Surgical probe devices in accordance with the present inventions preferably include a handle, a relatively short shaft, and one of the distal assemblies described hereafter in the catheter context. Preferably, the length of the shaft is about 4 inches to about 18 inches. This is relatively short in comparison to the portion of a catheter body that is inserted into the patient (typically from 23 to 55 inches in length) and the additional body portion that remains outside the patient. The shaft is also relatively stiff. In other words, the shaft is either rigid, malleable, or somewhat flexible. A rigid shaft cannot be bent. A malleable shaft is a shaft that can be readily bent by the physician to a desired shape, without springing back when released, so that it will remain in that shape during the surgical procedure. Thus, the stiffness of a malleable shaft must be low enough to allow the shaft to be bent, but high enough to resist bending when the forces associated with a surgical procedure are applied to the shaft.

A somewhat flexible shaft will bend and spring back when released. However, the force required to bend the shaft must be substantial.

II. Steerable Loop Structures

Figure 2:
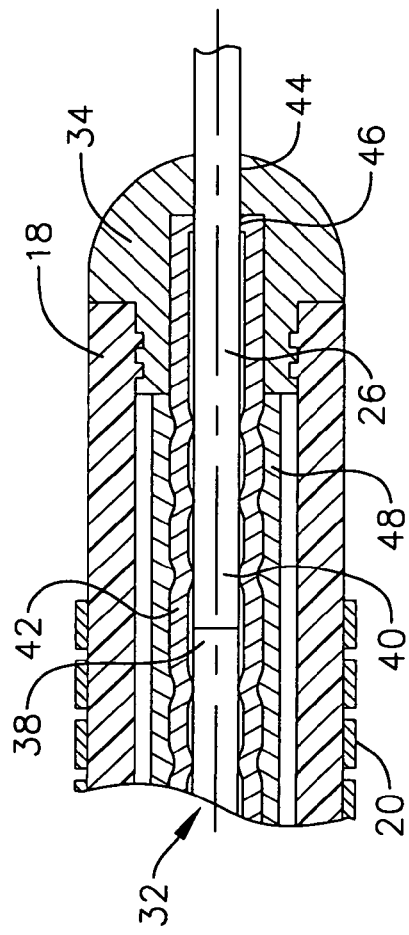
FIG. 2 is a section view of the distal end of the exemplary catheter illustrated in FIG. 1.

As illustrated for example in FIGS. 1 and 2, a catheter 10 in accordance with a preferred embodiment of a present invention includes a hollow, flexible catheter body 12 that is preferably formed from two tubular parts, or members. The proximal member 14 is relatively long and is attached to a handle 16, while the distal member 18, which is relatively short, carries a plurality of spaced electrodes 20 or other operative elements. The proximal member 14 is typically formed from a biocompatible thermoplastic material, such as a Pebax® material (polyether block emide) and stainless steel braid composite, which has good torque transmission properties. In some implementations, an elongate guide coil (not shown) may also be provided within the proximal member 14. The distal member 18 is typically formed from a softer, more flexible biocompatible thermoplastic material such as unbraided Pebax® material, polyethylene, or polyurethane. The proximal and distal members, which are about 5 French to about 9 French in diameter, are preferably either bonded together with an overlapping thermal bond or adhesively bonded together end to end over a sleeve in what is referred to as a "butt bond."

The catheter 10 is used in combination with a sheath 22, which preferably has a greater inherent stiffness than the distal region of the catheter 12 (i.e. the distal member 18, the electrodes 20 and a spline 32 that is discussed below with reference to FIGS. 4 and 5). The sheath 22 should also be lubricious to reduce friction during movement of the catheter body 12. With respect to materials, the sheath 14 is preferably a Pebax® and stainless steel braid composite. Other materials, such as polytetrafluoroethylene (PTFE), can also be used. The wall thickness of the sheath 22 is preferably about 0.013 inch, which will not add significantly to the overall thickness of the catheter 10. A handle 24, which is preferably in the form of a hemostatic connector that can be used to fix the relative positions of the catheter 12 and sheath 22, is mounted on the proximal end of the sheath.

In the exemplary embodiment illustrated in FIG. 1, the distal end of the sheath 22 is perpendicular to the longitudinal axis of the sheath. However, the distal end of the sheath 22 may also be cut at an angle and tapered in a transverse direction relative to the longitudinal axis of the sheath to effect the shape loop formed by the distal region of the catheter 12.

A pull wire 26 extends from the distal end of the catheter 12 through the sheath 22 in the exemplary embodiment illustrated in FIG. 1. The proximal end of the pull wire 26 includes an adjustable stop/handle 28. The pull wire 26 is preferably a flexible, inert cable constructed from strands of metal wire material, such as Nickel Titanium (commercially available under the trade name Nitinol®) or 17-7 stainless steel, that is about 0.012 to 0.018 inch in diameter. Alternatively, the pull wire 26 may be formed from a flexible, inert stranded or molded plastic material. The pull wire 26 is also preferably round in cross-section, although other cross-sectional configurations can be used.

Holding the handle 28 stationary, the physician deploys a loop structure 30 by advancing the catheter body 12 through the sheath 22. Once the loop structure 30 has been formed, the physician can pull on the wire 26 to decrease the exposed length of the pull wire beyond the distal end of the sheath 22. Further adjustments to the loop may be made by advancing or retracting the catheter body 12 within the sheath 22 or by putting tension on the pull wire 24. For example, a portion of the loop structure 30 my be bent out of the loop plane. This aspect of the invention is discussed in greater detail below with reference to FIGS. 5–9. In addition, the loop structure 30 can be rotated by rotating the catheter body 12 with its handle 16.

Figure 4:
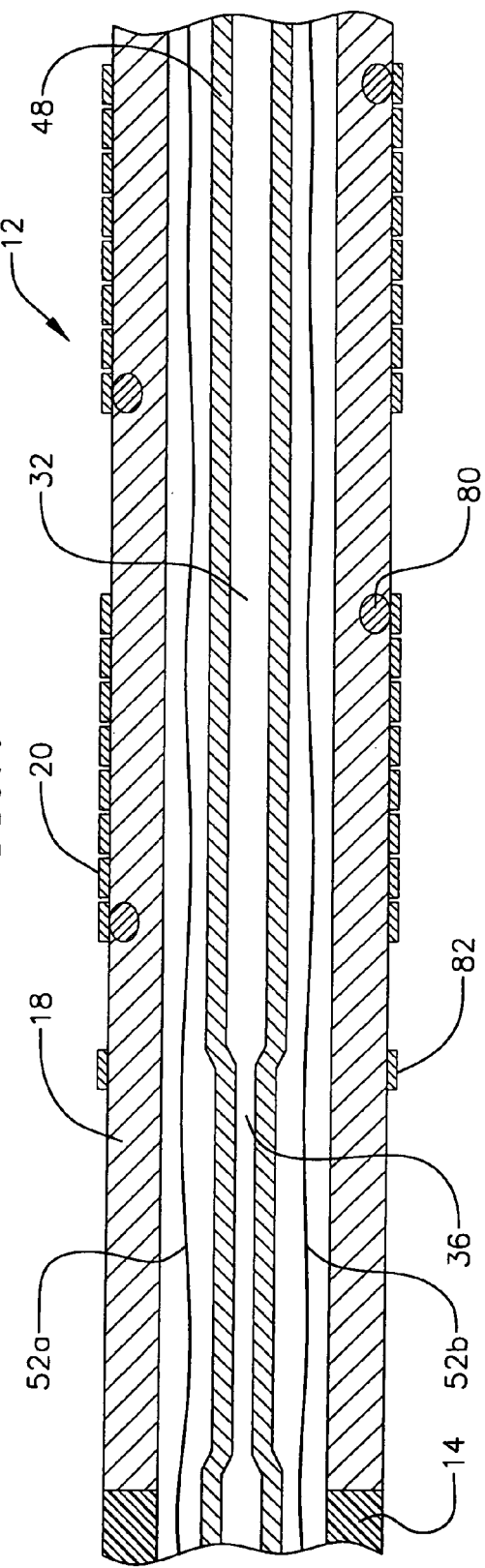
FIG. 4 is a section view of a portion of the distal region of the exemplary catheter illustrated in FIG. 1.

As illustrated in FIGS. 2 and 4, the exemplary catheter body 12 also includes a flexible spline (or "core wire") 32. The flexible spline 32 is preferably a wire having a diameter of approximately 0.023 inch that is positioned inside of and passes within the length of the catheter body 12. The flexible spline 32 is fixedly secured to the handle 16 at the proximal end of the catheter body 12 and to a tip member 34 in the manner described below. The tip member 34 is in turn secured to the distal end of the catheter body 12 with adhesive. In the preferred embodiment, the flexible spline 32 is made from resilient, inert wire, such as Nitinol® material or 17-7 stainless steel. Resilient injection molded plastic can also be used. The exemplary spline 32 is round in cross section, although other cross sectional configurations can be used. The flexible spline 32 may, if desired, also have a preset curvature accomplished by thermally presetting the spline at 500° C. for 8 minutes. The super-elastic properties of the material should, however, be maintained.

Figure 3:
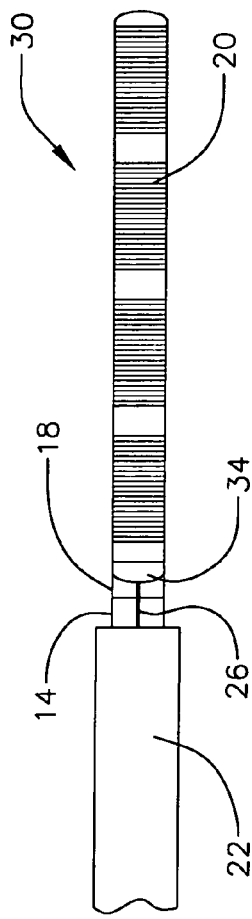
FIG. 3 is a top view of the distal region of the exemplary catheter illustrated in FIG. 1.

Referring more specifically to FIGS. 1, 3 and 4, the flexible spline 32 includes a flattened portion 36, which is preferably adjacent to (i.e. either just proximal to, just distal to, or aligned with) the proximal end of the distal member 18, that allows this portion of the flexible spline to be bent with less force than would otherwise be required. The flattened portion 36 also causes the distal member 18 to bend, and the loop structure 30 to be formed, in a flat loop plane (note the side view in FIG. 1 and the top view in FIG. 3). In an embodiment where the flexible spline 32 has a diameter of approximately 0.023 inch, the thickness of the flattened portion 36 would be about 0.018 inch and the length would be about 1.75 inches.

The flexible spline 32 may also be used to anchor the pull wire 26. As illustrated for example in FIG. 2, the distal end 38 of the flexible spline 32 is fixedly engaged in an in-line manner to the end 40 of the pull wire 26 with a stainless steel crimp tube 42. The in-line connection of the flexible spline 32 and pull wire 26 allows for a reduction in the overall diameter of distal portion of the catheter body 12. This provides a significant clinical advantage over devices having side by side pull wire connections which create a larger diameter device. The pull wire 26 passes through a pull wire bore 44 in the catheter tip member 24 and through a bore 46 in the distal end of the crimp tube 42.

The tip member 34 is preferably formed from platinum-iridium (90/10) and is fixedly engaged with, for example, silver solder, adhesive or spot welding, to the distal end of crimp tube 42. The flexible spline 32 is preferably electrically insulated with a thin walled polyester heat shrink tube 48 that extends beyond the proximal end of the crimp tube 42. Other pull wire configurations, other methods of attaching the pull wire to the catheter body, and methods of reducing stress on the pull wire are disclosed in U.S. Pat. No. 6,048,329, which is incorporated herein by reference.

The exemplary catheter 10 present also includes a loop deflection system that allows the physician to steer a portion 50 of the loop structure 30 out of the loop plane in the manner illustrated in FIGS. 6 and 7.

As illustrated in FIGS. 1 and 5, the steering capability may, for example, be provided through the use of one or more steering wires. The exemplary catheter 10 includes a pair of steering wires 52a and 52b which pass through the heat shrink tube 48 and are secured to the flexible spline 32 with a crimp joint, solder, adhesive or other suitable instrumentalities. Steering wires 52a and 52b extend proximally to the exemplary handle 16, which includes handle body 54 and a steering assembly 56 that consists of a cam wheel 58 and a lever 60. The proximal ends of each of the steering wires 52a and 52b are secured to a cam wheel 58. Tension is applied to steering wire 52a wire by urging the lever 60 proximally, while tension is applied to the steering wire 52b by urging the lever distally. Portion 50 in FIGS. 6 and 7 has been steered out of the loop plane by moving the lever in the clockwise direction and can be steered in the opposite direction by moving the lever in the counter-clockwise direction. Additional information concerning this type of handle is disclosed in U.S. Pat. No. 5,636,634. Other types of handles, such as piston and cylinder style handles, may also be employed.

The steering of portion 50 may be facilitated by forming a second flattened portion 62 in the spline 32 just proximally of the point at which the steering wires 52a and 52b are attached to the spline. The second flattened portion 62, which is rotated 90 degrees relative to the flattened portion 36, facilitates the steering of portion 50 by giving the bend directionality and creating a live hinge. In an embodiment where the flexible spline 32 has a diameter of approximately 0.023 inch, the thickness of the second flattened portion 62 would be about 0.010 inch and the length would be about 0.50 inch.

In an alternative embodiment, which is especially useful in situations that require a greater portion of the loop to be steered out of the loop plane, is illustrated in FIGS. 8 and 9. Steerable portion 50' is larger than the steerable portion 50 illustrated in FIGS. 6 and 7 because the second flattened portion (not shown) in the embodiment illustrated in FIG. 8 and 9 is longer than the second flattened portion 62 illustrated in FIG. 5. Here, a suitable length for the second flattened portion 62 in an embodiment where the flexible spline 32 has a diameter of approximately 0.023 inch would be about 1.5 inches.

The present inventions are also applicable to loop catheters in which the distal portion of catheter body is connected to the distal portion of the sheath. As illustrated for example in FIG. 10, the exemplary catheter 64 does not include a pull wire and instead is used in combination with a sheath 66 which has a distal member 68 that is connected to the distal end of the catheter 64. A slot is formed in the distal portion of the sheath 66 and the remnant 70 forms a flexible joint. A stiffening element 72 may also be provided. The loop 74 is formed when the catheter 64 is urged distally relative to the sheath 66, thereby causing the distal portion of the catheter to bulge outwardly in the manner illustrated in FIG. 10. Although not shown in FIG. 10, exemplary catheter 64 also includes the loop steering elements described above.

The loop steering elements described above may also be used in other loop catheters where the distal portion of catheter body is connected to the distal portion of the sheath. One example is a catheter wherein the distal end of the catheter body is connected to the distal end of a sheath by a short wire. This and other examples of such loop catheters are disclosed in U.S. Pat. No. 6,071,274, which is incorporated herein by reference.

In another alternative embodiment, and as illustrated for example in FIGS. 11–15, the steering wires 52a and 52b may be secured at respective points on the exterior of the catheter and then directed to respective points that are on the opposite side of the catheter. Such an arrangement provides more steering torque than would be realized if the steering wires were simply allowed to extend proximally from their attachment point in the manner illustrated in FIG. 5 because the present arrangement increases the effective lever length. This arrangement is also applicable to steerable catheters that are not adapted to be bent into loops as well as catheters with a single steering wire, whether adapted to be bent into a loop or not.

The exemplary catheter 84 illustrated in FIGS. 11–15 is in many respects identical to the catheter 10 illustrated in FIGS. 1–7. Here, however, the steering wires 52a and 52b are not secured to the spline 32. The steering wires 52a and 52b are instead directed through steering wire lumens 86a and 86b which are formed in the distal member 18'. The steering wire lumens 86a and 86b, which include respective inlets 88a and 88b and outlets 90a and 90b, each wind half way (i.e. 180 degrees) around the distal member 18'. The rotational position change measured as a function of longitudinal position change is preferably constant from one end of the steering wire lumens 86a and 86b to the other. Referring more specifically to FIG. 15, the inlets 88a and 88b and outlets 90a and 90b are also perpendicular to (i.e. offset 90 degrees from) the flattened surfaces of the second flattened portion 62. Although the exemplary distal member 18' could be formed by a multi-lumen extrusion process so if desired, the preferred process is a molding process. Here, core pins formed from flexible metal tubes could be used to form the steering wire lumens 86a and 86b.

The distal ends of the steering wires 52a and 52b extend outwardly through the outlets 90a and 90b and are secured to one of the electrodes 20 by, for example, welding or soldering. Alternatively, the steering wires 52a and 52b could be secured to a support ring (not shown) mounted on the exterior of the distal member 18'. A guide coil (not shown), or other tubular member though which the steering wires 52a and 52b would pass, may be positioned within the steering wire lumens 86a and 86b to provide additional column strength.

In an alternative implementation, the steering wire lumens 86a and 86b would be eliminated and replaced by channels formed in the outer surface of the distal member 18'. The channels would extend around the distal member in the same manner as the steering wire lumens 86a and 86b and the inlets 88a and 88b would simply extend through the wall of the distal member 18' to the proximal ends of the channels. Guide coils, or other tubular members through which the steering wires 52a and 52b pass, would be positioned within the channels. The electrodes 20 would be placed over the channels and guide coils.

III. Electrodes, Temperature Sensing and Power Control

In each of the preferred embodiments, the operative elements are a plurality of spaced electrodes 20. However, other operative elements, such as lumens for chemical ablation, laser arrays, ultrasonic transducers, microwave electrodes, and ohmically heated hot wires, and such devices may be substituted for the electrodes.

The spaced electrodes 20 are preferably in the form of wound, spiral coils. The coils are made of electrically conducting material, like copper alloy, platinum, or stainless steel, or compositions such as drawn-filled tubing (e.g. a copper core with a platinum jacket). The electrically conducting material of the coils can be further coated with platinum-iridium or gold to improve its conduction properties and biocompatibility. A preferred coil electrode is disclosed in U.S. Pat. No. 5,797,905. The electrodes 20 are electrically coupled to individual wires (not shown) to conduct coagulating energy to them. The wires are passed in conventional fashion through a lumen extending through the associated catheter body into a PC board in the catheter handle, where they are electrically coupled to a connector 76 that is received in a port on the handle. A connector 78 may be plugged into a source of RF coagulation energy and/or an electrophysiology recording system for mapping.

As an alternative, the electrodes may be in the form of solid rings of conductive material, like platinum, or can comprise a conductive material, like platinum-iridium or gold, coated upon the device using conventional coating techniques or an ion beam assisted deposition (IBAD) process. For better adherence, an undercoating of nickel or titanium can be applied. The electrodes can also be in the form of helical ribbons. The electrodes can also be formed with a conductive ink compound that is pad printed onto a non-conductive tubular body. A preferred conductive ink compound is a silver-based flexible adhesive conductive ink (polyurethane binder), however other metal-based adhesive conductive inks such as platinum-based, gold-based, copper-based, etc., may also be used to form electrodes. Such inks are more flexible than epoxy-based inks.

The flexible electrodes 20 are preferably about 4 mm to about 20 mm in length. In the preferred embodiment, the electrodes are 12.5 mm in length with 1 mm to 3 mm spacing, which will result in the creation of continuous lesion patterns in tissue when coagulation energy is applied simultaneously to adjacent electrodes. For rigid electrodes, the length of the each electrode can vary from about 2 mm to about 10 mm. Using multiple rigid electrodes longer than about 10 mm each adversely effects the overall flexibility of the device, while electrodes having lengths of less than about 2 mm do not consistently form the desired continuous lesion patterns.

The portion of the electrodes 20 that are not intended to contact tissue (and be exposed to the blood pool) may be masked through a variety of techniques with a material that is preferably electrically and thermally insulating. This prevents the transmission of coagulation energy directly into the blood pool and directs the energy directly toward and into the tissue. For example, a layer of UV adhesive (or another adhesive) may be painted on preselected portions of the electrodes to insulate the portions of the electrodes not intended to contact tissue. Deposition techniques may also be implemented to position a conductive surface only on those portions of the assembly intended to contact tissue. Alternatively, a coating may be formed by dipping the electrodes in PTFE material.

The electrodes may be operated in a uni-polar mode, in which the soft tissue coagulation energy emitted by the electrodes is returned through an indifferent patch electrode (not shown) externally attached to the skin of the patient. Alternatively, the electrodes may be operated in a bi-polar mode, in which energy emitted by one or more electrodes is returned through other electrodes. The amount of power required to coagulate tissue ranges from 5 to 150 w.

As illustrated for example in FIG. 4, a plurality of temperature sensors 80, such as thermocouples or thermistors, may be located on, under, abutting the longitudinal end edges of, or in between, the electrodes 20. Preferably, the temperature sensors 80 are located at the longitudinal edges of the electrodes 20. In some embodiments, a reference thermocouple 82 may also be provided. For temperature control purposes, signals from the temperature sensors are transmitted to the source of coagulation energy by way of wires (not shown) that are also connected to the aforementioned PC board in the catheter handle. Suitable temperature sensors and controllers which control power to electrodes based on a sensed temperature are disclosed in U.S. Pat. Nos. 5,456,682, 5,582,609 and 5,755,715.

In those instances where the ultimate orientation of a catheter relative to tissue (i.e. which side faces the tissue) is unpredictable, such as when a catheter with a pull wire is used, the temperature sensors 80 may be located on two sides of catheter, as illustrated in FIG. 4. Alternatively, in those instances where the orientation is more predictable, such as when the catheter is secured to the distal end of the sheath, the temperature sensors may all be located on the same side of the catheter, as illustrated in FIG. 10. Here, the temperature sensors will be preferably located within a linear channel (not shown) that is formed in the distal member 18. The linear channel insures that the temperature sensors will directly face the tissue and be arranged in linear fashion. Such an arrangement results in more accurate temperature readings which, in turn, results in better temperature control. As such, the actual tissue temperature will more accurately correspond to the temperature set by the physician on the power control device, thereby providing the physician with better control of the lesion creation process and reducing the likelihood that embolic materials will be formed. Such a channel may be employed in conjunction with any of the electrode (or other operative element) supporting structures disclosed herein.

The electrodes 20 and temperature sensors 80 can include a porous material coating, which transmits coagulation energy through an electrified ionic medium. For example, as disclosed in U.S. Pat. No. 5,991,650, electrodes and temperature sensors may be coated with regenerated cellulose, hydrogel or plastic having electrically conductive components. With respect to regenerated cellulose, the coating acts as a mechanical barrier between the surgical device components, such as electrodes, preventing ingress of blood cells, infectious agents, such as viruses and bacteria, and large biological molecules such as proteins, while providing electrical contact to the human body. The regenerated cellulose coating also acts as a biocompatible barrier between the device components and the human body, whereby the components can now be made from materials that are somewhat toxic (such as silver or copper).

Although the present inventions have been described in terms of the preferred embodiments above, numerous modifications and/or additions to the above-described preferred embodiments would be readily apparent to one skilled in the art. It is intended that the scope of the present inventions extend to all such modifications and/or additions and that the scope of the present inventions is limited solely by the claims set forth below.

We claim:

1. A probe for use with an outer member including a wall defining an interior bore and a distal end, the probe comprising:

an elongate body, defining a distal region, a distal end, a proximal region and an interior, adapted to be carried within the outer member interior bore;

at least one operative element supported on the distal region of the elongate body;

a connector adapted to connect the distal end of the elongate body to the distal end of the outer member such that a loop will be formed when the elongate body is moved distally relative to the outer member; and a steering element extending within the interior of the elongate body from the distal region of the elongate body to the proximal region of the elongate body and secured to the distal region of the elongate body such that proximal movement of the steering element will deflect a portion of the loop relative to the remainder of the loop.

2. A probe as claimed in claim 1, wherein the steering element comprises a pair of steering elements.

3. A probe as claimed in claim 1, wherein the elongate body comprises a catheter body.

4. A probe as claimed in claim 1, wherein at least the distal region of the elongate body includes a flexible spline.

5. A probe as claimed in claim 4, wherein the flexible spline comprises a solid core wire.

6. A probe as claimed in claim 4, wherein the flexible spline defines a substantially circular cross sectional shape over a substantial portion thereof and a substantially flat cross sectional shape over a relatively small portion thereof.

7. A probe as claimed in claim 4, wherein the steering element is fixedly secured to the flexible spline.

8. A probe as claimed in claim 4, wherein the flexible spline includes a first flattened portion and a second flattened portion that is rotationally offset from the first flattened portion.

9. A probe as claimed in claim 8, wherein the second flattened portion is rotationally offset from the first flattened portion by 90 degrees.

10. A probe as claimed in claim 1, wherein the operative element comprises an electrode.

11. A probe as claimed in claim 1, wherein
the loop defines a loop plane; and
the steering element is secured to the distal region of the elongate body such that proximal movement of the steering element will deflect a portion of the loop out of the loop plane without substantially bending the remainder of the loop out of the loop plane.

12. A probe as claimed in claim 1, wherein the proximal region of the elongate body is relatively long and stiff and the distal region of the elongate body is relatively short and flexible.

13. A probe as claimed in claim 1, wherein the connector is integral with the outer member.

14. A probe as claimed in claim 1, wherein
the at least one operative element comprises a plurality of operative elements supported on a portion of the distal region of the elongate body; and
the steering element is secured to the elongate body within the portion of the distal region on which the plurality of operative elements are supported.

15. A probe as claimed in claim 14, wherein the plurality of operative elements comprises a plurality of electrodes.

16. A probe, comprising:
an elongate body defining a distal region and a proximal region;
at least one operative element supported on the distal region of the elongate body; and
a steering element secured at a first side of the distal region of the elongate body and extending to a second side of the distal region opposite the first side of the distal region and from the second side of the distal region to the proximal region of the elongate body.

17. A probe as claimed in claim 16, wherein the distal portion of the elongate body defines a steering wire lumen extending from the first side to the second side.

18. A probe as claimed in claim 16, wherein the first side is offset from the second side by 180 degrees.

19. A probe as claimed in claim 16, wherein the steering wire is secured to the at least one operative element.

20. A probe as claimed in claim 16, wherein at least a portion of the steering element is longitudinally aligned with the at least one operative element.

* * * * *